United States Patent [19]
Baldwin

[11] 3,941,128
[45] Mar. 2, 1976

[54] FLUID DISPENSING ARRANGEMENT

[75] Inventor: Brian E. Baldwin, Wilmette, Ill.

[73] Assignee: Affiliated Hospital Products, Inc., St. Louis, Mo.

[22] Filed: Oct. 18, 1974

[21] Appl. No.: 515,966

Related U.S. Application Data

[63] Continuation of Ser. No. 359,265, May 11, 1973, abandoned, which is a continuation of Ser. No. 88,360, Nov. 10, 1970, abandoned.

[52] U.S. Cl. .......................................... 128/218 NV
[51] Int. Cl.² ........................................... A61M 5/00
[58] Field of Search .... 128/218 R, 218 NV, 218 M, 128/272, 220, 276, 218 P, 218 D, 215, DIG. 28; 222/387; 215/6; 206/219; 141/27

[56] References Cited
UNITED STATES PATENTS

| | | | |
|---|---|---|---|
| 2,538,662 | 1/1951 | Abbott | 128/218 NV |
| 2,607,341 | 8/1952 | Brown | 128/218 NV |
| 2,610,628 | 9/1952 | Lockhart | 128/272 |
| 2,893,390 | 7/1959 | Lockhart | 128/218 NV |
| 3,075,525 | 1/1963 | McConnaughey | 128/218 NV |
| 3,076,456 | 2/1963 | Hunt, Sr. | 128/218 M |
| 3,102,539 | 9/1963 | Goldberg | 128/218 NV |
| 3,136,440 | 6/1964 | Krug et al. | 128/DIG. 5 |
| 3,207,374 | 9/1965 | Holmes et al. | 128/272 UX |
| 3,330,282 | 7/1967 | Visser et al. | 128/218 M |
| 3,373,743 | 3/1968 | Saffir | 128/218 NV |
| 3,397,694 | 8/1968 | Ogle | 128/218 M X |
| 3,467,097 | 9/1969 | Ogle | 128/DIG. 28 |
| 3,674,028 | 7/1972 | Ogle | 128/DIG. 28 |

*Primary Examiner*—John D. Yasko
*Attorney, Agent, or Firm*—Reginald F. Pippin, Jr.

[57] ABSTRACT

A fluid dispensing arrangement for injecting liquid parenteral drugs or other liquids, including a syringe or cartridge with a needle-hub secured thereto, a plunger in the syringe or cartridge for effecting liquid discharge and injection, and a combination sealing and by-pass valve plug initially in a radially compressed sealing position at the forward end of the cartridge or syringe body or barrel and separating the liquid in the cartridge or syringe body or barrel from the needle-hub assembly, the valve plug being longitudinally forwardly movable to a by-pass discharge position within a by-pass chamber of larger diameter than the normal unrestricted and uncompressed diameter of the plug. The plug has tapered cruciform ends with corresponding circumferentially spaced by-pass grooves formed thereby at its opposite ends to aid in liquid by-pass therepast during liquid discharge or aspirating action.

22 Claims, 7 Drawing Figures

BRIAN E. BALDWIN
INVENTOR

ATTORNEY

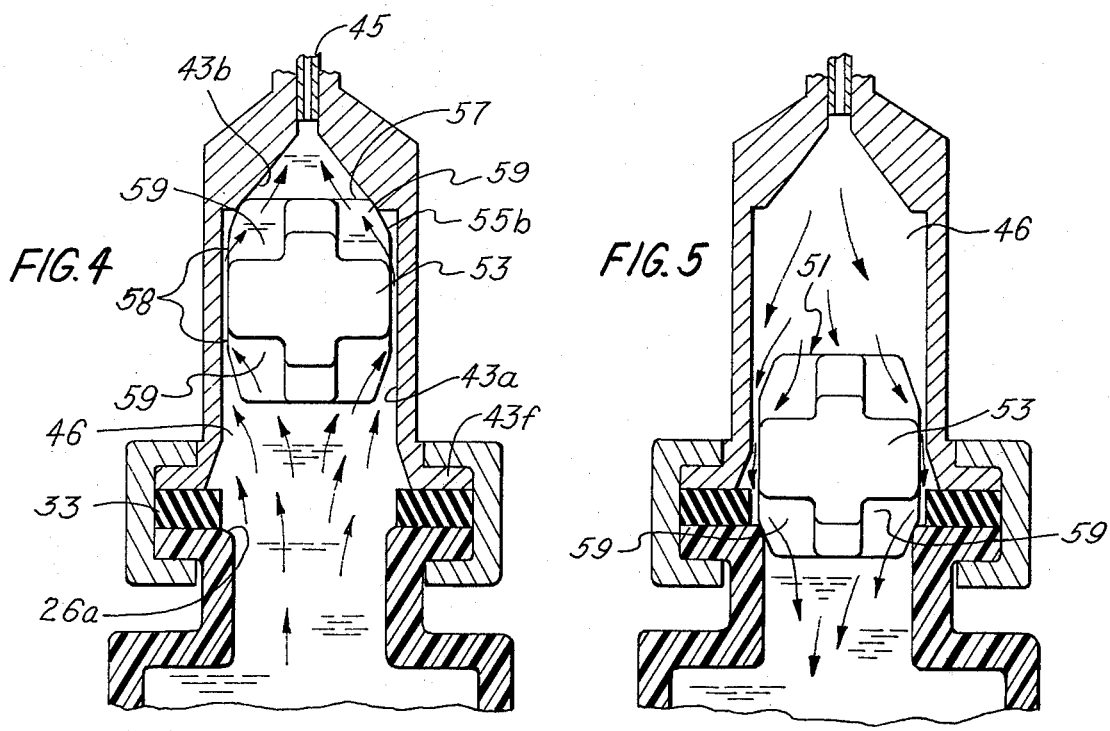
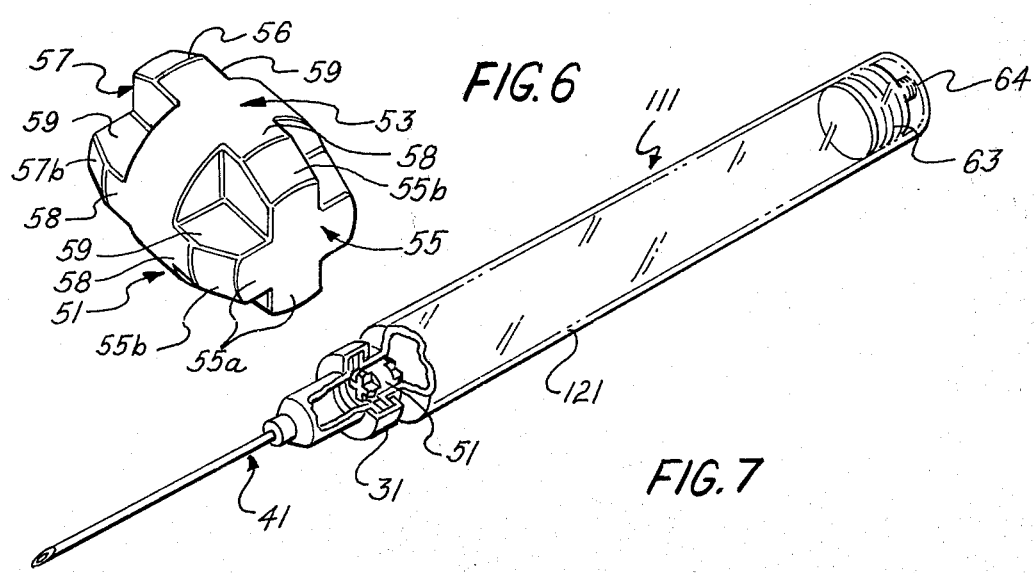
BRIAN E. BALDWIN
INVENTOR
ATTORNEY

FLUID DISPENSING ARRANGEMENT

This is a continuation of application Ser. No. 359,265 filed May 11, 1973, now abandoned which in turn is a continuation of application Ser. No. 88,360 filed Nov. 10, 1970, now abandoned.

This invention relates to a fluid dispensing arrangement which is particularly adapted for prefilled manufacture and storage in a ready condition for use by an operator for injection of parenteral liquids, or other desired liquids, into a human body or other living organism.

One of the major problems in packaging liquid parenteral drugs into prefilled syringes or cartridges is that of the incompatibility of most drug products with any and all metal ions. Since it is normally necessary to ultimately pass drug solutions through a metal needle or cannula during the injection of such liquids, it is necessary to protect the liquid from the needle until the time of use, to thereby prevent or effectively minimize degradation of the liquid. There have been numerous attempts to develop arrangements which would solve this problem, including various diaphragm and valve arrangements. However, to my knowledge all such prior arrangements have had substantial drawbacks and difficulties associated therewith.

In one prior art arrangement, which has a number of different forms, a double ended (i.e., double pointed) needle is attached in some suitable way to a syringe or cartridge, and until such is to be used the butt end of the needle is held in a position slightly removed from a rubber diaphragm which in turn seals off the liquid in the syringe or cartridge from the needle-hub assembly. When ready for use, the syringe or cartridge is activated by forcing the butt end of the needle through the rubber diaphragm, thus permitting the liquid to pass through the needle when pressure is applied to a sliding rubber plunger which is seated in the glass cartridge body or syringe barrel. Among the disadvantages of this system or arrangement is the fact that this requires the puncturing of a diaphragm, and any time a rubber stopper or diaphragm is punctured by a hollow needle or cannula, there arises the possibility of coring, which can carry dangerous rubber particles into the body. In addition, there is the further disadvantage of poor economics, caused by the increase in cost of providing butt end grinding of the needle in addition to the normal forward end bevel grinding of the needle.

In another prior art arrangement, the needle or cannula is initially passed through and held in a rubber diaphragm or rubber stopper, and the forward end of the needle is then sealed from the atmosphere by embedding such into a removable rubber sheath. This, however, does not completely protect the parenteral liquid from contact with the needle, but merely reduces the surface area of the needle in contact with the liquid.

There is also a prior art arrangement employing two spaced plungers in a glass syringe or cartridge, with a needle-hub assembly secured to the glass syringe or cartridge body. In this arrangement the plunger innermost or nearmost the needle-hub assembly has two small skin flaps which are cut approximately 270° around their diameter. When pressure is applied by moving the outer most plunger through thumb action thereon, the liquid between the two plungers passes through these skin flaps and out through the needle of the needle-hub assembly and into the body into which fluid is being injected. A substantial disadvantage of this type of system is the extremely close tolerances necessary in the molding and trimming operation required for this arrangement, particularly the plunger with the skin flaps. In addition, this arrangement does not provide an absolute seal between the liquid and the needle-hub assembly.

In a further prior art arrangement, a needle-hub assembly is assembled to a glass cartridge, and the fluid in the cartridge is protected from the needle-hub assembly by a rubber stopper having a thin diaphragm formed in the radially center section of the stopper. When the rear plunger of the cartridge is moved forward under thumb pressure, the fluid acts as a force transmitting element to exert a rupturing force on the rubber diaphragm and thereby balloons the diaphragm into the needle-hub assembly until the diaphragm ruptures and thereby permits the liquid to pass into and through the needle-hub assembly. An obvious disadvantage of this arrangement is the requirement for extremely tight tolerances to be maintained in the manufacture of the rubber stopper with its thin diaphragm. In addition, there is the distinct possibility of rubber particulate matter being broken loose from the ruptured portion of the rubber stopper diaphragm section and the corresponding discharge of such through the needle-hub assembly into the body receiving the injection.

A further prior art arrangement utilizes a molded rubber stopper between the glass vial or cartridge body and the needle-hub assembly, with a small glass ball fitted within a longitudinal bore extending through the rubber stopper. The small glass ball is initially seated in the stopper bore, being held within an enlarged recess portion of the bore, and upon forward acting pressure being exerted on the ball by forward motion of the rear plunger within the cartridge body, the ball will pop out of the stopper bore, thereby permitting the liquid to pass through the stopper bore, by-passing the free glass ball within the needle-hub assembly, and thereupon proceeding through the needle and into the body being injected. Among the disadvantages of this arrangement is the necessity for molding the rubber stopper and the formation of the glass ball to extremely tight tolerances, as well as the necessity for trimming the internal diameter of the bore in the zone where it accepts the ball. There is also the need for use of a relatively hard durometer rubber compound in order to preserve the configuration of the rubber stopper while the ball is in its sealed position. There is also the inability in this arrangement of preventing the glass ball from reseating itself back into the rubber stopper bore during aspiration action, and in addition, there is the need to double-bevel the butt end of the needle in order to keep the ball from sealing off the small diameter bore of the needle.

It is accordingly an object and feature of the present invention to provide a simple and economical syringe or cartridge arrangement with a needle-hub assembly thereon, which enables full protection of the injectible parenteral drug or other liquid from contact with the metal parts of the needle-hub arrangement, and for that matter from any metal parts of the syringe or cartridge, until such time as the syringe or cartridge is to be used.

It is a further feature to provide such an arrangement through utilization of a longitudinally movable combination sealing and by-pass valve plug which may be formed of ordinary pharmaceutical grade rubber compounds, and which does not require a precise durometer or formulation of the rubber for its successful operation, other than that it be an effectively non-reactive material as to the liquid in the syringe or cartridge, and that it be sufficiently soft and elastic to enable its elastically compressive retention in a sealed position and condition within the mouth of a cartridge vial body or syringe barrel or body made of glass or other desired material, while not so spongy soft as to deform in response to liquid flow thereagainst to an extent such as to effect closure of either of the fluid flow orifices with which it comes into contact in the by-pass condition.

It is a further feature of the invention to provide such an arrangement which will enable both initial pre-use sealing of the liquid and subsequent discharge and multiple aspirating flow of the liquid, as may be desired, during injection or aspirating action by the operator.

It is still a further feature of the invention to provide such an arrangement which permits the construction of a needle-hub assembly from materials which normally are excluded from the construction of needle-hub assemblies in other prefilled syringe or cartridge arrangements, including aluminum, various plastics, and other materials which are considered to be compatible on short term contact with drugs or other parenteral fluids, but not necessarily compatible for long term contact therewith.

There is also the added feature and advantage of the invention in alleviating any necessity for precise or difficult trimming operations on the movable valve plug, as is often the case in prior art constructions as noted above.

Still other objects, features and attendant advantages will become apparent to those skilled in the art from a reading of the following detailed description of a preferred physical embodiment constructed in accordance with the invention, taken in conjunction with the accompanying drawings wherein:

FIGS. 4 and 5 are longitudinal section views similar to FIG. 3, illustrating respectively the general position of the combination sealing and by-pass valve plug in its forwardmost and rearwardmost positions within the by-pass chamber and during respectively injection and aspirating liquid flow therepast.

FIG. 6 is an enlarged view in perspective, illustrating the combination sealing and by-pass valve plug configuration.

FIG. 7 is a modified arrangement similar to that of FIG. 1, taking the form of a cartridge unit which may be inserted into a syringe body adapted to receive conventional needle-hub combined cartridge units.

Figure 1:
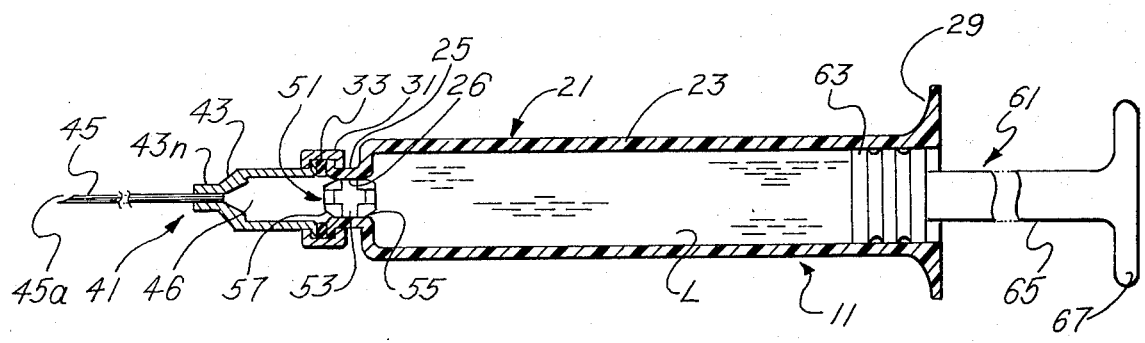
FIG. 1 is a longitudinal section view of a syringe arrangement constructed according to the invention, the arrangement being shown in the prefilled sealed condition.

Referring now in detail to the figures in the drawings, a physical embodiment of the invention is shown in FIG. 1, in the form of a pre-fillable sealed syringe unit generally indicated at 11, including a syringe body or barrel 21, to which is secured a needle-hub assembly 41, with a discharge plunger 61 axially movable within the syringe barrel 21.

The syringe barrel 21 takes the form of a vial or cartridge type body of glass or other suitable material, including a cylindrical main body section 23 which is open at its rear end to receive the discharge plunger 61. A laterally extending finger-grip flange 29 may be secured to or formed on the barrel 21 to enable ease of handling during liquid discharge and injection or aspiration operation of the syringe. Obviously other finger-grip arrangements may be employed, various finger-grip arrangements of this nature being available and common in the art.

Figure 2:
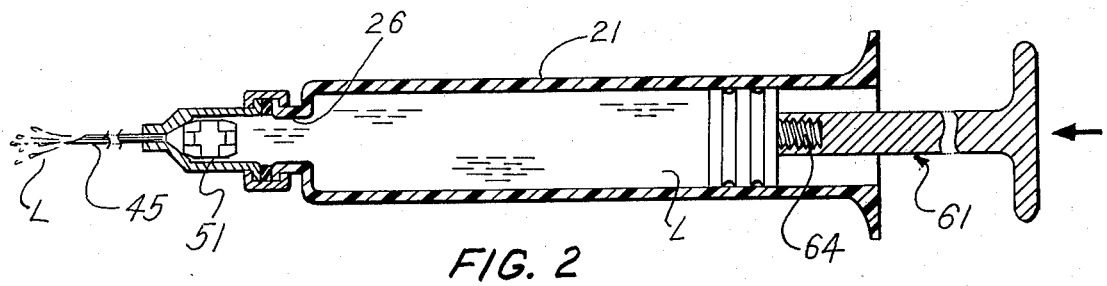
FIG. 2 is a view similar to that of FIG. 1, and illustrating the general position of the parts during discharge of liquid from the syringe needle, and also as such would be related during injection into a body.

The discharge plunger 61 includes a piston 63 which may be suitably formed of pharmaceutical grade rubber and may take any conventional or desired configuration to effect a fluid tight seal with the inner wall of the barrel 21 and thereby enable movement of the liquid L in discharge or aspirating fashion from or into the liquid holding chamber formed by the barrel 21. The discharge plunger 61 also includes a plunger rod 65 which may be suitably secured to the rubber piston 63, as through the medium of a threaded connection therebetween, as indicated at 64 in FIG. 2. Plunger rod 65 may have a suitably flared thumb engaging end 67 for forward or rearward actuation of the piston 63 by the operator.

The barrel 21 is formed with a reduced diameter neck 25 at its forward end, which defines a liquid discharge mouth 26 having a central cylindrical configuration which may be rounded or tapered or beveled at one or both of its opposite longitudinal ends, as indicated generally at 26a in FIG. 4. The forward neck end of the body or barrel 21 has an annular securing lip flange 27 formed thereon. The needle-hub assembly 41 is secured to the body or barrel 21 through the medium of a ring or sheath connector 31 which may be suitably crimped about the annular periphery of the annular lip 27 and the hub flange 43f, and with a suitable ring seal 33 such as a ring washer or "O" ring of rubber or other suitable resilient material extending in interfacing relation between the hub flange 43f and the annular lip flange 27, to provide a liquid tight seal connection. The ring or sheath connector 31 may be formed of easily worked metal, such as aluminum or other desired material. Likewise, inasmuch as the hub 43 and cannula 45 of the needle-hub assembly 41 does not stand in contact with the liquid L in the syringe body or barrel 21 during the period prior to use, it will be appreciated that the cannula 45 and hub 43 may be formed of desired metallic or plastic materials which fit the normal use requirements therefor, and which are suitable for short term contact with the liquid L to be injected. The hub 43 may thus be formed of aluminum or plastic as normally desired materials, and the cannula 45 may be formed of steel or plastic or other suitable material as may be desired. Cannula 45 may be suitably secured at its butt end 45b within the forward nose or neck end 43n of the hub 43, and the pointed forward end 45a of the cannula 45 may be suitably pointed as by conventional bevel grinding. If desired, the forward nose or neck end 43n and the hub 43 may be formed with an external configuration adapted to engage in male interfitting relation with a female Luer connector, such that if desired, an operator may break off the cannula 45 at the nose 43n, and insert the nose 43n into a Luer connector for dispensing through another user arrangement connected to the Luer connector in a given instance of use.

In the initial prefilled condition of the syringe unit 11, a combination sealing and by-pass valve plug 51 is disposed in liquid sealing relation within the mouth 26, as shown in FIG. 1. This plug 51 is preferably formed as a unitary body, and may be suitably formed of rubber material of a pharmaceutical grade. Plug 51 has a sealing midsection 53 which is cylindrical and of a normal radially uncompressed diameter slightly greater than the internal cylindrical diameter of the mouth 26, within which the sealing midsection 53 is radially compressibly seated in the initial sealing prefilled condition of the syringe. In this respect, it will be noted, as shown in FIG. 1, that in the initial prefilled condition the rubber piston 63 is disposed near the rear end of the syringe barrel 21, with liquid being contained between the plug 51 and the piston 63, thereby providing an effective fluid tight sealing of the liquid L within the barrel 21. Inasmuch as the barrel 21 may be formed of pharmaceutically acceptable glass and the plug 51 and piston 63 may be formed of a pharmaceutical grade rubber, it will therefore be appreciated that the liquid L is thereby held in a prefilled stored condition which will substantially eliminate or maintain to a minimal degree any reaction between the container and the liquid L during the stored condition, which may extend over a substantial period of time.

The combination sealing and by-pass valve plug 51 has an effectively undulating end surface which at its opposite ends are non-complementary to the opposite ends of by-pass chamber 46 formed forward of the mouth 26. The effectively undulating end surfaces of the plug 51 are formed to enable fluid by-pass past the plug 51 after the plug has been moved forward out of the mouth 26 and into the by-pass chamber 46, independent of whether the plug is in contact with one or the other of the ends of the chamber 46 or is in the zone therebetween. In the preferred and illustrative embodiment, the effective undulating end configuration is formed as a tapered cruciform configuration, as indicated at 55 and 57. The cruciform shaped ends 55 and 57 include radial cross elements 55a and 57a which form therebetween by-pass grooves 59 on opposite longitudinal ends of the cylindrical sealing end section 53 of the plug. The cruciform shaped ends 55 and 57 are tapered as indicated at 55b and 57b, the tapered portions extending only part way along the axially longitudinal extent of the radial cross elements 55a,57a of the cruciform ends, thus leaving a less tapered or straight longitudinal surface 58 connecting with the cylindrical surface of the sealing midsection 53. The provision of this straight or less tapered surface 58 on the cruciform cross elements 55a,57a aids in assuring against closure of the by-pass grooves 59 when either of the respective tapered and cruciform portions 55b, 57b of ends 55, 57 is in engagement with a respective one of the opposite ends of the by-pass chamber 46. Prevention of closure of the by-pass grooves 59 is also aided by forming the taper angle of the end portions 55b,57b of the plug differently from the taper of the tapered forward end surface 43b of the hub interior as well as the rounded or beveled mouth entrance 26a at the opposite ends of the by-pass chamber 46. As an aid to ease of molding of the plug 51, the various edges may be slightly beveled or rounded, as generally indicated at 56 in FIG. 6, if so desired, this rounding or beveling also aiding in minimizing any requirements for trimming after molding.

Figure 3:
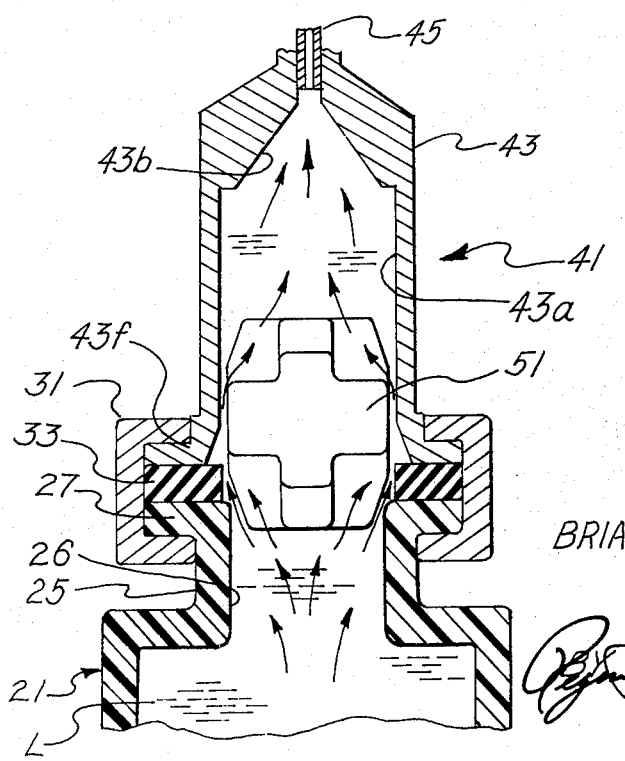
FIG. 3 is an enlarged section view of the forward section of the syringe, illustrating the position of the sealing and by-pass plug substantially immediately upon its movement from its sealing position to a free by-pass position within the mouth of the cartridge vial body or syringe barrel or body.

As is shown in FIGS. 3–5, the plug 51 is formed with an effective normal uncompressed outer diameter which is sufficiently less than the internal diameter of the by-pass chamber 46 as formed by the hub interior wall 43a, to enable effective liquid flow past the plug 51 while the plug is in the by-pass chamber 46. In addition, it is desirable to form the plug 51 with an overall effective longitudinal diagonal extent substantially greater than the internal cross-sectional diameter of the hub interior wall 43a, so as to prevent the plug 51 from undesirably canting and locking within the by-pass chamber 46, although with the provision of the cruciform ends and by-pass grooves 59, this canting will not normally close off the flow of liquid past the plug 51 within the by-pass chamber 46.

In operation, the operator grasps the syringe 11 and presses the discharge plunger 61 forwardly to eject a small amount of liquid L from the needle or cannula 45, in the same manner as the operator would normally operate a syringe in this respect. In enabling this discharge of liquid L from the cannula 45 with the present invention, the forward motion of the rubber piston 63 will effect through the liquid L a forward pressure and force on the plug 51 to thereby move the plug out of the mouth 26 and into the enlarged diameter by-pass chamber 46. The plug 51 will be aided in this forward motion into the by-pass chamber 46 by the forward camming motion of the rear tapered end surface 55b thereof as it proceeds out of the rounded mouth entrance 26a, although in general the forward fluid pressure on the plug 51 will be sufficient to effect the full discharge of the plug 51 from the mouth 26. The liquid L will open travel through the mouth 26 and past the plug 51, through the by-pass chamber 46, and out through the interior of the cannula 45. Continued forward motion of the rubber piston 63 will effect sufficient fluid flow to cause the plug 51 to engage the forward tapered end surface 43b of the by-pass chamber 46, in which event the liquid L will continue to flow past the plug 51, passing through the by-pass grooves 59, while the forward tapered end of the plug 51 is in engagement with the tapered end surface 43b. Upon insertion of the cannula 45 into a body for injection of the liquid L into the body, the operator may desire to effect aspiration by rearward motion of the discharge plunger 61. This is readily enabled with the present invention, as the flow of liquid can and will proceed rearwardly from the patient's body and through the cannula 45, into the by-pass chamber 46, and past the plug 51, and subsequently into the chamber formed within the barrel 21, permitting the operator to view the aspirated material from the body. This rearward or aspirating motion of fluid through the hub 43 and into the barrel 21 may effect rearward motion of the plug 51 to a degree such that the plug will come into contact at its rearward end with the rounded mouth entrance of the mouth 26. In such event, it will be noted that, as shown in FIG. 5, the fluid will again flow about and past the midsection 53 of the plug and through the by-pass grooves 59, through the mouth 26 and into the central chamber holding the liquid L in the barrel 21. Thereupon, the operator may proceed with the injection of the liquid L into the patient's body, with liquid L again flowing forwardly through the cannula 45 as a function of forward motion of the discharge plunger 61 by the operator's manual action thereon. Subsequent aspirating may be effected at any time as the operator may desire, with further subsequent injection, without fear of stopping flow of the liquid into or out of the barrel 21 and cannula 45.

In FIG. 7 there is shown a modified embodiment, in which a sealed fluid discharge unit 111 takes the form of a cartridge unit which may be inserted into a syringe adapted to receive cartridge units having needle hub assemblies affixed thereto. In this arrangement, the liquid to be injected is held in prefilled condition within a body or barrel 121 of glass or other suitable material, which again is preferably transparent or translucent, with a rear discharge plunger piston 63 having a threaded connector stud 64 for connection to a plunger rod of a syringe into which the cartridge unit 111 is inserted. The body or barrel 121 does not have a finger grip section 29 as in the previously described embodiment, as the syringe shell or body will be provided with such as may be desired and as in conventional construction. The body or barrel 121 is otherwise formed as in the previously described embodiment of the barrel 21 of FIG. 1, with a plug 51 within the forward mouth thereof, and with a needle hub assembly 41 secured to the forward end of the body or barrel 121 as through the medium of a connector ring 31. The operation of this embodiment is similar to that of FIG. 1 except that the cartridge is inserted into a syringe body which is adapted for receiving such cartridge units, and does not itself form a complete syringe, although such might be formed by adding a removable finger-gripping unit for securing to the rear end of the barrel or body 121, and using a discharge plunger rod 65, such as in FIG. 1.

While the invention has been described with respect to several illustrative, preferred embodiments thereof, it will be appreciated by those skilled in the art that various modifications and improvements may be made without departing from the scope and spirit of the invention. Accordingly, the invention is not to be limited by the illustrative embodiment, but only by the scope of the appended claims.

That which is claimed is:

1. For use in an arrangement adapted to have a dispensable liquid therein, with a manually operated plunger for injecting said liquid into a body, the improvement comprising:

a liquid-carrying body having adjacent its forward end a mouth, a central liquid-holding chamber, and an opposite open end for receiving said plunger to effect movement of liquid to or from said chamber and through said mouth, a manually operated plunger slidable in said chamber to effect movement of liquid to or from said chamber and through said mouth, said body having a dispensing end forward of said mouth, a combination sealing and by-pass valve plug having a radially compressible, relatively soft elastic midsection initially seated within and sealing said mouth in a radially elastically compressed condition of the plug, a by-pass chamber and associated connecting liquid discharge opening formed forward of said mouth, said by-pass chamber having forward and rear liquid-passageway-forming ends, said forward liquid-passageway-forming end forming a portion of said dispensing end of said body, said by-pass chamber being larger in internal cross-section than said mouth and larger in all cross-sectional directions in cross-sectional chamber extent than the respective corresponding elastically free or released effective external sealing configuration of said plug and having an effective combined longitudinal and cross-sectional extent of sufficient amount whereby said plug will have freedom of movement in both longitudinal and lateral directions when ejected to its free condition into said chamber, said plug having a second displaced free position and condition in said by-pass chamber, in which second position and free condition said plug is smaller than the corresponding cross-section in all cross-sectional directions of said by-pass chamber and larger in effective cross-section than said mouth, the opposite ends of said plug being non-complementarily shaped relative to the opposite longitudinal ends of said by-pass chamber, so as to enable liquid to pass therepast when the plug is in end engagement with either the forward or rear end of said by-pass chamber, after removal of the plug from its sealing position within said mouth and into said by-pass chamber, said plug being of a normal cross-section in its elastically free or relaxed condition sufficiently greater than said mouth of said body to prevent, in conjunction with one of its non-complementarily shaped ends, reverse movement thereof back into sealing relation within said mouth as a function of reverse or aspirating flow of liquid therepast.

2. An arrangement according to claim 1, said plug having longitudinal end surfaces irregular to enable fluid to pass therepast when in end engagement with either the needle hub or the forward mouth of said body after disengagement of said plug from its sealing position within said mouth.

3. An arrangement according to claim 1, said plunger being initially slidably disposed in sealing relation in said body chamber and rearwardly of said plug and said forward mouth.

4. An arrangement according to claim 1, said body being a vial of a cartridge unit fittable within a syringe.

5. An arrangement according to claim 1 and comprising a syringe, said body being a syringe barrel.

6. An arrangement according to claim 1, further comprising
 a prefilled liquid within said liquid-holding chamber, and a plunger slidably disposed in sealing relation within said liquid-holding chamber and extending through opposite open end of said body.

7. An arrangement according to claim 1, said plug having a tapered irregular surfaced end section on at least one end thereof, the irregularities thereof forming corresponding fluid passage grooves, and said tapered irregular surfaced end section on said plug being non-complementary to the respective interfacing end portion of said by-pass chamber when said plug is freed from its restricted sealing position within said mouth.

8. An arrangement according to claim 7, said plug having a said tapered and irregular surfaced end section on both longitudinal ends thereof.

9. An arrangement according to claim 8, said tapered and irregular surfaced end sections having a cruciform shape in cross-section and being formed by intersecting cross elements transversely extending out from a common central hub and all connecting with said midsection.

10. An arrangement according to claim 9, the effective axial longitudinal extent of said cruciform end cross elements being longer than the effective axial longitudinal extent of said tapered outer end surface thereof, to aid in preventing resealing of said plug with said mouth as a function of aspirating or reverse liquid flow thereagainst, as well as preventing sealing action through plug contact at the opposite end of said chamber.

11. An arrangement according to claim 8, said body having a needle hub assembly, said needle-hub assembly including a hub section having a forwardly pointed cannula extending therefrom, said hub having a tapered inner end wall adjacent the inner end of said cannula and forming the forward end of said by-pass chamber, the taper of said tapered inner end wall of said hub being different from the taper of the respective interfacing end of said plug.

12. An arrangement according to claim 1, said body having a reduced diameter neck portion forming said open mouth, said mouth and said plug midsection being generally circular in cross-section.

13. An arrangement according to claim 12, said body being formed as a syringe barrel having a laterally extending finger gripping section at the rear thereof.

14. An arrangement according to claim 13, said plug midsection being generally circular but larger in uncompressed diameter than said generally circular mouth, said plug being smaller in diameter than at least a corresponding length of said chamber formed forward of said mouth, and being longer than the internal cross-section of said by-pass chamber.

15. For use in an arrangement adapted to have a dispensable liquid therein and which utilizes a manually operated plunger for dispensing liquids, the improvement comprising:

a liquid-carrying body having at its forward end a mouth, a central liquid-holding chamber, and an opposite open end for receiving said plunger to effect movment of liquid to or from said chamber and through said mouth, a combination sealing and by-pass valve plug having a radially compressible, relatively soft elastic midsection initially seated within and sealing said mouth in a radially elastically compressed condition of the plug, a by-pass chamber and associated connected fluid discharge opening formed forward of said mouth, said by-pass chamber being larger in internal cross-section than said mouth and larger in all directions of cross-sectional chamber extent than the respective corresponding elastically free released external configuration of said plug whereby said plug will have freedom of movement in all lateral directions when effectively fully ejected into said chamber from its sealing condition in said mouth, the opposite ends of said plug being non-complementarily shaped relative to the opposite longitudinal ends of said by-pass chamber, so as to enable liquid to pass therepast when the plug is in end engagement with either the forward or rear end of said by-pass chamber, after removal of the plug from its sealing position within said mouth and into said by-pass chamber, said plug being of a normal cross-section in its elastically free released condition sufficiently greater than said mouth of said body to prevent, in conjunction with one of its said non-complementarily shaped ends, reverse movement thereof back into sealing relation within said mouth as a function of reverse or aspirating flow of liquid therepast.

16. An arrangement for dispensing liquids, according to claim 15, the rear zone of said plug being elastic and having a tapered external surface smaller at its rear extremity than at the forward end of such tapered surface, a portion of said tapered rear surface being larger in elastically free released condition than the effective forward exit end zone of said mouth, whereby said plug is aided in passage forward through the forward exit end of said mouth by the combined action of the compressive forces within the laterally compressed plug and acting to restore the plug to an unstressed released state and the camming surface interaction between the tapered external surface of said plug and the forward end of said mouth, said tapered external surface aiding in preventing sealing re-entry and sealing seating of said plug into said mouth as a result of aspirating liquid flow action on said plug.

17. For use in an arrangement adapted to have a dispensable liquid therein and which utilizes a manually operated plunger for dispensing liquids, the improvement comprising:

a body having a liquid-holding chamber with a forward mouth, said chamber including a section for movement of said plunger therealong to effect movement of liquid to or from said chamber and through said mouth, a combination sealing and by-pass valve plug having a radially compressible, relatively soft elastic midsection initially seated within and sealing said mouth in a radially elastically compressed condition of the plug, a by-pass chamber formed forward of said mouth and larger in internal cross-section than said mouth and larger in cross-sectional chamber extent than the respective corresponding elastically free released external configuration of said plug, the opposite ends of said plug being non-complementarily shaped relative to the opposite longitudinal ends of said by-pass chamber, so as to enable liquid to pass therepast when the plug is in end engagement with either the forward or rear end of said by-pass chamber, after removal of the plug from its sealing position within said mouth and into said by-pass chamber, said plug being of a normal cross-section in its elastically free released condition sufficiently greater than said mouth of said body to prevent, in conjunction with one of its said non-complementarily shaped ends, reverse movement thereof back into sealing relation within said mouth as a function of reverse or aspirating flow of liquid therepast.

18. An arrangement for dispensing liquids, according to claim 17, the rear zone of said plug being elastic and having a tapered external surface smaller at its rear extremity than at the forward end of such tapered surface, a portion of said tapered rear surface being larger in elastically free released condition than the effective forward exit end zone of said mouth, whereby said plug is aided in passage forward through the forward exit end of said mouth by the combined action of the compressive forces within the laterally compressed plug and acting to restore the plug to an unstressed released state and the camming surface interaction between the tapered external surface of said plug and the forward end of said mouth, said tapered external surface aiding in preventing sealing re-entry and sealing seating of said plug into said mouth as a result of aspirating liquid flow action on said plug.

19. For use in an arrangement adapted to have a dispensable liquid therein and which utilizes a manually operated plunger for dispensing liquids, the improvement comprising:

a liquid-carrying body having at its forward end a mouth, a central liquid-holding chamber, and an opposite open end for receiving a plunger to effect movement of liquid to or from said chamber and through said mouth, a combination sealing and by-pass valve plug having a radially compressible, relatively soft elastic midsection initially seated within and sealing said mouth in a radially elastically compressed condition of the plug, a by-pass chamber and associated connected liquid discharge opening formed forward of said mouth, said by-pass chamber being larger in internal cross-section than said mouth and the elastically expanded cross-section of said plug, the opposite ends of said plug being non-complementarily shaped relative to the opposite longitudinal ends of said by-pass chamber, so as to enable liquid to pass therepast when the plug is in end engagement with either the forward or rear end of said by-pass chamber, after removal of the plug from its sealing position within said mouth and into said by-pass chamber, said plug being of a normal cross-section in its elastically free released condition sufficiently greater than said mouth of said body to prevent reverse movement thereof back into sealing relation within said mouth as a function of reverse or aspirating flow of the liquid therepast, the rear zone of said plug being elastic and having a tapered external surface smaller at its rear extremity than at the forward end of such tapered surface, a portion of said tapered rear surface being larger in elastically free released condition than the effective forward exit end zone of said mouth, whereby said plug is aided in passage forward through the forward exit end of said mouth by the combined action of the compressive forces within the laterally compressed plug and acting to restore the plug to an unstressed released state and the camming surface interaction between the tapered external surface of said plug and the forward end of said mouth, said tapered external surface aiding in preventing sealing, re-entry and sealing seating of said plug into said mouth as a result of aspirating liquid flow action on said plug.

20. An arrangement for dispensing liquid comprising:

a syringe body having a substantially constant diameter bore forming a liquid-holding chamber, said bore chamber being adapted for movement of a plunger therealong, a plunger slidably movable in said bore chamber to effect movement of liquid to or from said chamber and through said mouth, a combination sealing and by-pass valve plug having a radially compressible, relatively soft elastic midsection initially seated within and sealing said mouth in a radially elastically compressed condition of the plug, a step-enlargement annular by-pass chamber formed forward of said mouth and larger in internal cross-section than said mouth and the elastically expanded cross-section of said plug, and having a liquid discharge opening adjacent its forward end zone, the opposite ends of said plug being non-complementarily shaped relative to the opposite longitudinal ends of said by-pass chamber, so as to enable liquid to pass therepast when the plug is in end engagement with either the forward or rear end of said by-pass chamber, after removal of the plug from its sealing position within said mouth and into said by-pass chamber, said plug being of a normal cross-section in its elastically free released condition greater than said mouth of said body to prevent, in conjunction with one of its non-complementarily shaped ends, reverse movement thereof back into sealing relation within said mouth as a function of reverse or aspirating flow of liquid therepast, the rear zone of said plug being elastic and having a tapered external surface smaller at its rear extremity than at the forward end of such tapered surface and smaller than at the forward end of the cross-sectional configuration of said mouth, a portion of said tapered rear surface being larger in elastically free released condition than the effective forward exit end zone of said mouth, whereby said plug is aided in passage forward through the forward exit end of said mouth by the combined action of the compressive forces within the laterally compressed plug and acting to restore the plug to an unstressed released state and the camming surface interaction between the tapered external surface of said plug and the forward end of said mouth, said tapered external surface aiding in preventing sealing re-entry and sealing seating of said plug into said mouth as a result of aspirating liquid flow action on said plug.

21. An arrangement according to claim 20, said by-pass chamber having a tapered forward end wall in which is formed said fluid discharge opening, the taper of said tapered forward end wall of said by-pass chamber being different from the taper of the respective interfacing forward end of said plug.

22. An arrangement according to claim 21, said by-pass chamber being larger in internal cross-section in all lateral directions than said mouth and than the elastically free released external configuration of said plug when said plug is fully disposed therein.

* * * * *